(12) United States Patent
Miranda et al.

(10) Patent No.: US 7,191,013 B1
(45) Date of Patent: Mar. 13, 2007

(54) HAND HELD DEVICE FOR WIRELESS POWERING AND INTERROGATION OF BIOMEMS SENSORS AND ACTUATORS

(75) Inventors: Felix Antonio Miranda, Olmsted Falls, OH (US); Rainee N Simons, North Olmsted, OH (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 61 days.

(21) Appl. No.: 10/983,230

(22) Filed: Nov. 8, 2004

(51) Int. Cl.
*A61N 1/00* (2006.01)

(52) U.S. Cl. .................................................. 607/60
(58) Field of Classification Search ................ 607/30, 607/31, 60–63; 604/65; 600/546
See application file for complete search history.

(56) References Cited

U.S. PATENT DOCUMENTS

| | | | |
|---|---|---|---|
| 4,006,748 A | 2/1977 | Schulman | |
| 5,621,422 A | 4/1997 | Wang | |
| 5,646,633 A | 7/1997 | Dahlberg | |
| 5,683,434 A | 11/1997 | Archer | |
| 5,800,494 A | 9/1998 | Campbell et al. | |
| 5,861,019 A | 1/1999 | Sun et al. | |
| 6,009,350 A | 12/1999 | Renken | |
| 6,137,453 A | 10/2000 | Wang et al. | |
| 6,353,443 B1 | 3/2002 | Ying | |
| 6,411,842 B1* | 6/2002 | Cigaina et al. | 600/546 |
| 6,463,329 B1 | 10/2002 | Goedeke | |
| 6,667,725 B1 | 12/2003 | Simons et al. | |
| 2001/0016683 A1 | 8/2001 | Darrow et al. | |
| 2002/0027531 A1 | 3/2002 | Brown et al. | |
| 2002/0042637 A1 | 4/2002 | Stover | |
| 2002/0058906 A1* | 5/2002 | Lebel et al. | 604/65 |
| 2002/0123777 A1 | 9/2002 | Dolgin et al. | |
| 2002/0177884 A1 | 11/2002 | Ahn et al. | |
| 2005/0267550 A1* | 12/2005 | Hess et al. | 607/60 |

* cited by examiner

*Primary Examiner*—George Manuel
(74) *Attorney, Agent, or Firm*—Arlene P. Neal; Kent N. Stone

(57) ABSTRACT

A compact, hand-held device for wireless powering, interrogation and data retrieval from at least one implanted sensor. The hand-held device includes an antenna for powering an implanted sensor and for receiving data from the implanted sensor to the hand-held device for at least one of storage, display or analysis. The hand-held device establishes electromagnetic coupling with a low radiating radio frequency power inductor in the implanted sensor at a predefined separation and the antenna geometry allows for the antenna to power, interrogate and retrieve data from the implanted sensor without strapping the hand-held device to a human body housing the implanted sensor The hand-held device optionally allows for activation of the implanted sensor only during interrogation and data retrieval.

20 Claims, 10 Drawing Sheets

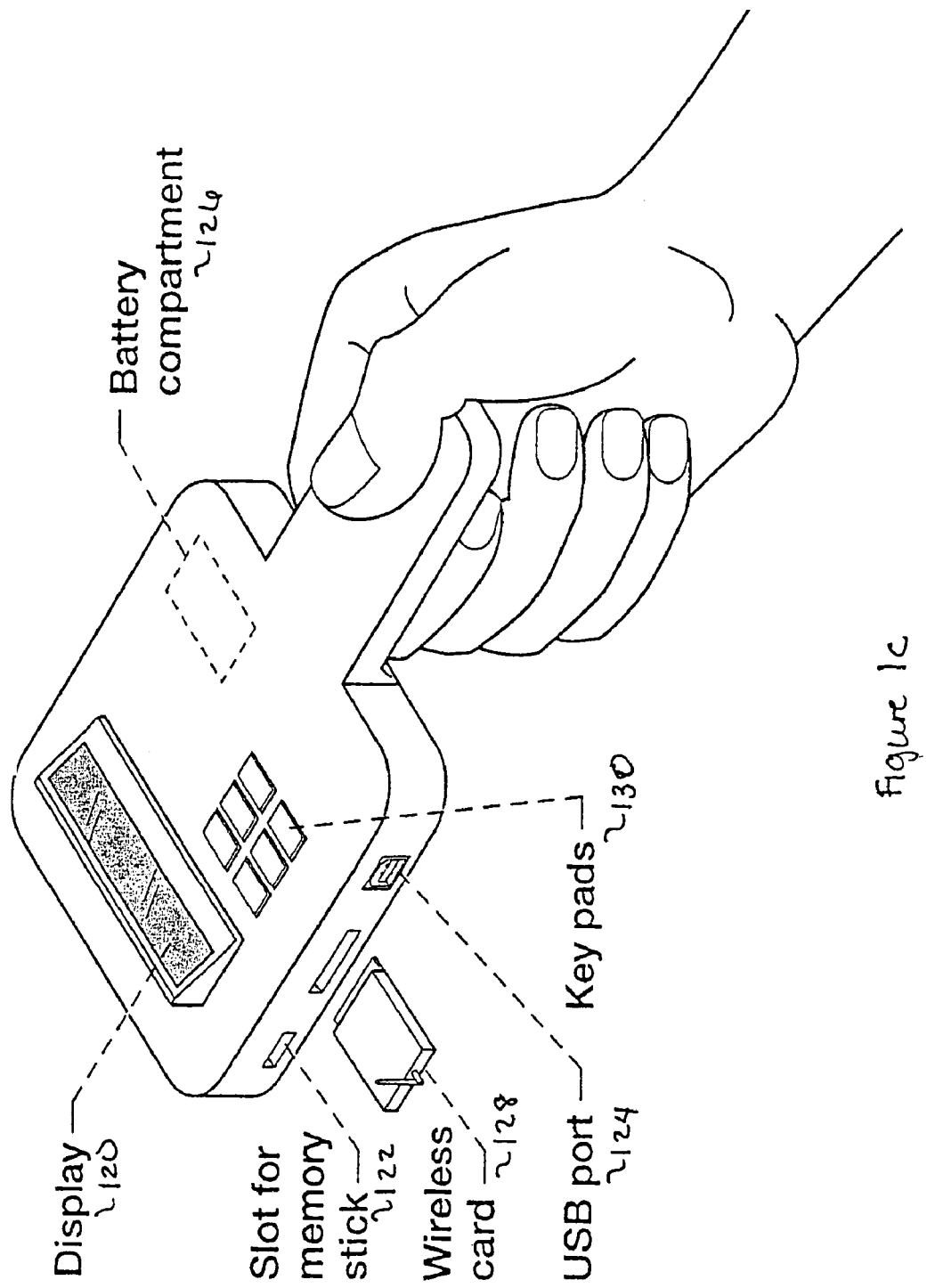

HAND HELD DEVICE FOR WIRELESS POWERING AND INTERROGATION OF BIOMEMS SENSORS AND ACTUATORS

FIELD OF THE INVENTION

The present invention relates to a telemetry based implantable sensing system for monitoring the physiological parameters of humans and particularly to a compact, reliable hand-held device for contactless-powering, interrogation and data retrieval via radio frequency (RF) telemetry from miniaturized biosensors that are embedded in a human body for medical diagnostics.

BACKGROUND OF THE INVENTION

Some of the conventional sensors that are used in biomedical implants require powering through batteries and lead wires. For example, a prior wireless telemetry technique for measuring the pressure and temperature in a fetus, uses an implantable pill shaped transmitter that transmits in pulse interval modulation and is battery powered. An external receiver converts the received RF signal into a digital pulse stream which is decoded into pressure and temperature data. The transmission range for the transmitter is 3 to 6 feet.

A disadvantage with sensors that require powering through batteries and lead wire is that the embedded sensing circuit is always on and power dissipates in the biological tissue. This causes local heating and shortens the life span of the sensor. Additionally, sensors powered through batteries and lead wires require that at least the batteries be implanted in the body. This increases the possibility of infection due to the potential for leakage from the batteries. Furthermore, sensors powered by batteries and lead wires require shielding from moisture and the lead wires reduce the mobility of the person with the implantable sensor.

Other known sensors are remote powering and monitoring equipments. However these sensors are typically bench scale and not portable. In one known system for measuring induced vibrations in hip prosthesis, an implanted transmitter is a Resistance-Inductance-Capacitance (RLC) series resonant circuit that transmits in Pulse Code Modulation (PCM) format. The transmitter is inductively powered and an external receiver circuit for receiving the transmitted signal is a tuned amplifier. In another known system for measuring force and temperature in a hip prosthetic head, the implantable transmitter is a single Negative-Positive-Negative (NPN) transistor coupled to a one-turn loop antenna. The transmitter is inductively powered and the external receiver is a loop antenna with an integrated amplifier strapped around the leg.

The disadvantage with known sensors that are battery-less is the typical requirement that an external receiving circuit that consists of localized external protuberance be strapped to the body of a patient/user or that a distributed circuit approach be implemented in a wearable vest. Both of these approaches limit the freedom of motion of the user performing ordinary daily activities, such as jogging or swimming. Depending on the location of the sensor and the type of diagnosis, the external sensor worn on the user could also impact the self esteem of the user. Furthermore, some systems with battery-less sensors are designed for close range proximity, i.e. the external receiving circuit is placed in direct contact with the skin.

SUMMARY OF THE INVENTION

According to one aspect of the invention, there is provided a compact, hand-held device for wireless powering, interrogation and data retrieval from at least one implanted sensor. The hand-held device includes an antenna for powering an implanted sensor and for receiving data from the implanted sensor to the hand-held device for at least one of storage, display or analysis. The hand-held device establishes electromagnetic coupling at radio frequency with an inductor in the implanted sensor at a predefined separation and allows for the antenna to power, interrogate and retrieve data from the implanted sensor without strapping the hand-held device to a human body housing the implanted sensor.

According to another aspect of the invention, there is provided a method for obtaining a reading in a hand-held device from at least one implanted sensor. The method includes the step of emitting a pulse from an external hand-held device within a predefined proximity to a receptor in an implanted sensor, wherein the pulse is used for at least one of powering and interrogating the implanted sensor. The method also includes the steps of powering the implanted sensor by inducing a voltage, via the pulse, in an inductor embedded in the implanted sensor and retrieving energy radiated by the inductor as a telemetry signal by an antenna in the hand-held device. The method further includes the step of receiving data, by the antenna, from the implanted sensor to the hand-held device for at least one of storage, display or analysis.

According to another aspect of the invention, there is provided a hand-held device for wireless powering, interrogation and data retrieval from at least one implanted sensor. The hand-held device includes an antenna for powering an implanted sensor and for retrieving data from the implanted sensor to the hand-held device for at least one of storage, display or analysis. The antenna includes an integrated amplifier to enable communications across larger implant depths, integrated surface mount inductors for impedance tuning of the antenna and at least one signal processing mechanism. The hand-held device establishes electromagnetic coupling at radio frequency with an inductor in the implanted sensor at a predefined separation and an antenna geometry allows for the antenna to power, interrogate and retrieve data from the implanted sensor without strapping the hand-held device to a human body housing the implanted sensor.

According to another aspect of the invention, there is provided a hand-held device for wireless powering, interrogation and data retrieval from at least one implanted sensor. The hand-held device includes a multi-turn loop antenna printed on a dielectric substrate. The antenna is used for powering an implanted sensor and for receiving data from the implanted sensor to the hand-held device for at least one of storage, display or analysis. The antenna includes an integrated amplifier to enable communications across larger implant depths, integrated surface mount inductors for impedance tuning of the antenna and at least one signal processing mechanism. The hand-held device establishes electromagnetic coupling at radio frequency with an inductor in the implanted sensor at a predefined separation and the antenna geometry allows for the antenna to power, interrogate and retrieve data from the implanted sensor without strapping the hand-held device to a human body housing the implanted sensor.

According to another aspect of the invention, there is provided an apparatus for obtaining a reading in a hand-held device from at least one implanted sensor. The apparatus includes emitting means for emitting a pulse from an external hand-held device within a predefined proximity to a receptor in an implanted sensor. The pulse is used for at least one of powering and interrogating the implanted sensor. The apparatus also includes powering means for powering the implanted sensor by inducing a voltage, via the pulse, in an inductor embedded in the implanted sensor. The apparatus further includes receiving means for receiving energy radiated by the inductor as a telemetry signal by an antenna in the hand-held device and receiving means for receiving data, by the antenna, from the implanted sensor to the hand-held device for at least one of storage, display or analysis.

BRIEF DESCRIPTION OF THE DRAWINGS

The accompanying drawings, which are included to provide a further understanding of the invention and are incorporated in and constitute a part of this specification, illustrate embodiments of the invention that together with the description serve to explain the principles of the invention.

In the drawings:

FIG. 1c further illustrates the hand-held device;

DESCRIPTION OF EMBODIMENTS

Reference will now be made in detail to the preferred embodiments of the present invention, examples of which are illustrated in the accompanying drawings. The present invention described below extends the functionality of a hand-held device for an implantable sensor. The hand-held device is a compact working system, having minimal impact on a human with an implanted biosensor, for powering the in-vivo biosensor and for obtaining data from the in-vivo sensor via telemetry, wherein the obtained data may be further analyzed and processed on an external system.

Figure 1A:
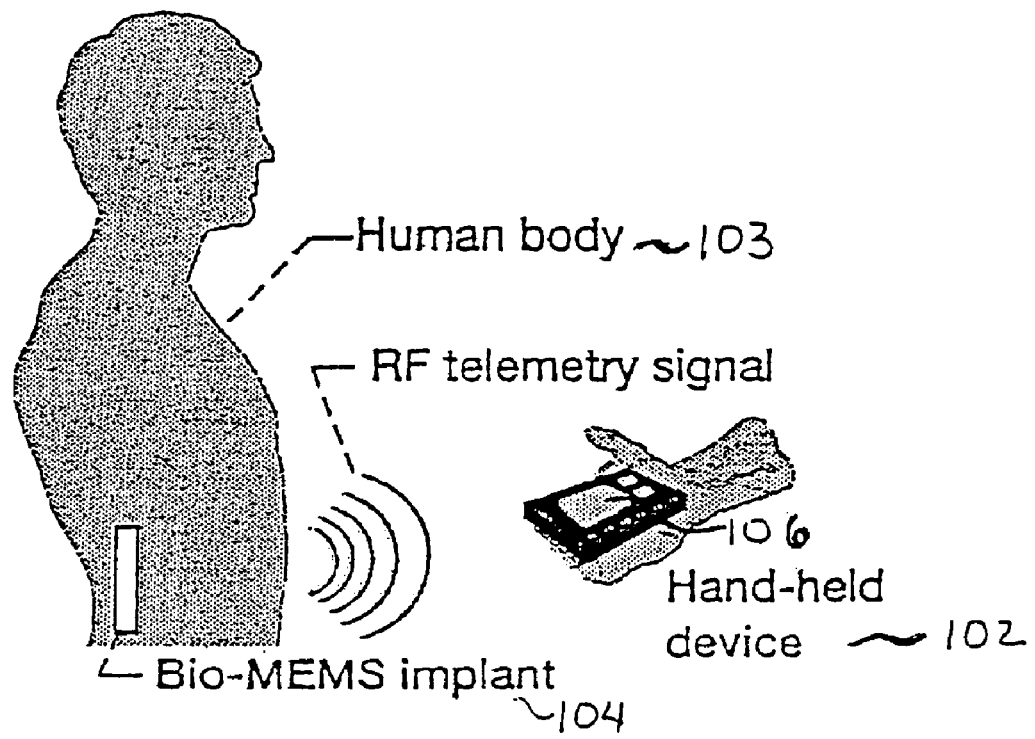
FIG. 1a illustrates a portable, palm-sized, hand-held device for wireless powering, interrogation and data retrieval from at least one biosensor imbedded in the body for medical diagnosis.

FIG. 1a illustrates a portable, palm-sized, hand-held device 102 for wireless powering, interrogation and data retrieval from at least one biosensor 104 imbedded in a human body 103 for medical diagnosis. Hand-held device 102 includes an antenna 106, which is further illustrated in FIG. 1b, for inductively powering implanted sensor 104 through a typical amount of body fluid and tissue. Antenna 106 is also used for receiving data from sensor 104 to hand-held device 102 for storage, display and/or analysis. Antenna 106 is capable of picking up signals that are vertically, horizontally as well as slant (45°) polarized. Hand-held device 102 also includes well known supporting electronic circuitry for data logging, display and downloading to a data storage and retrieval unit.

Figure 1B:
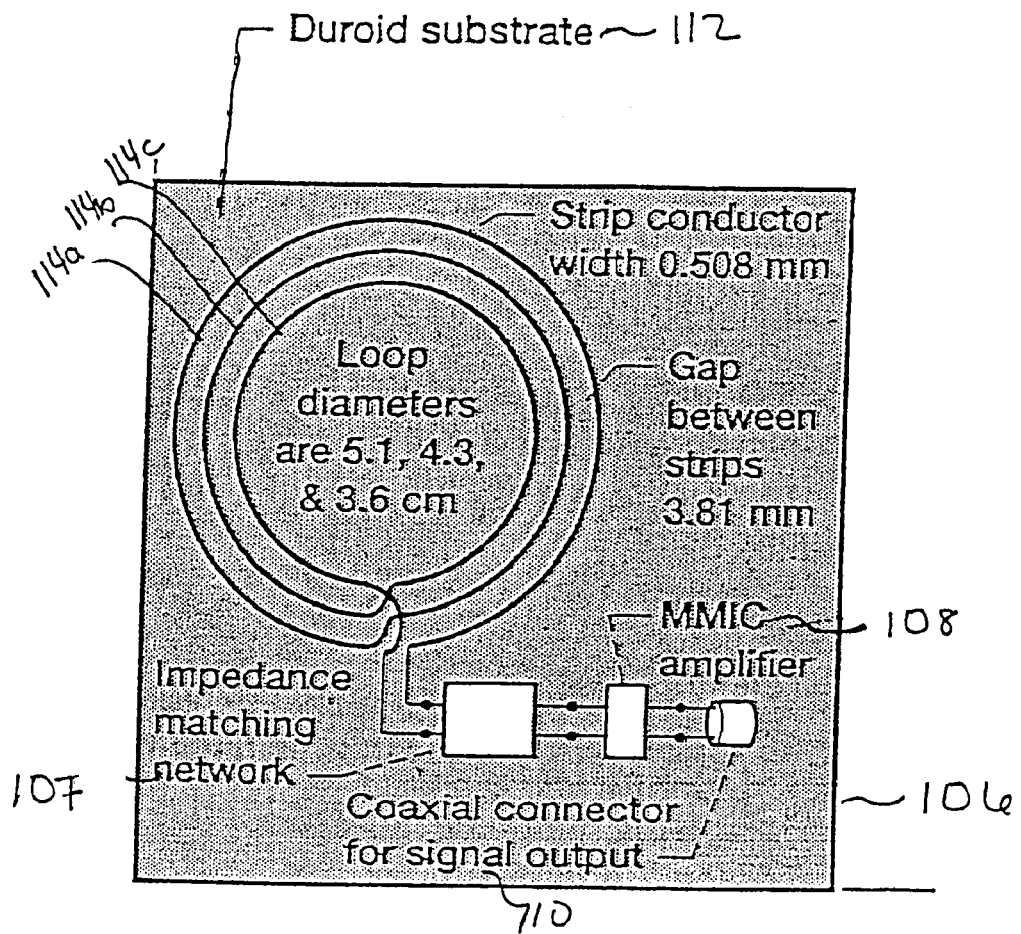
FIG. 1b illustrates the antenna in the hand-held device.

As shown in FIG. 1b, antenna 106 acts as a receive antenna during interrogation mode, wherein antenna 106 picks-up RF radiation as a telemetry signal from miniaturized transmitting source 104 when antenna 106 is placed in close proximity to an emitter inside the human body where the emitter is located. An MMIC amplifier 108 has been integrated with pick-up antenna 106 to enable communications across larger implant depths. Antenna 106 has integrated surface mount inductors for impedance tuning of the antenna. Antenna 106 also includes signal output mechanism 110, such as a coaxial connector. According to an embodiment of the invention, antenna 106 is a printed multi-turn loop antenna whose input impedance at about 330 MHz is matched, by impedance matching network 107, to input impedance of a MMIC low noise amplifier chip in a receiver to increase sensitivity. The diameter 114a, 114b and 114c of multi-turn loop antenna 106 is small, thus enabling hand-held device 102 to be very compact.

Multi-turn loop antenna 106 is printed, using known printed circuit fabrication techniques, on a substrate 112 with a central annular region. This facilitates the housing of signal processing circuits and thus lowers the height and profile of packaged hand-held device 102. Substrate 112 consists of a low loss RF dielectric substrate, such as Duroid®, fused quartz or alumina of the order of 30 mils thick. The method used in the invention to fabricate antenna 106 on dielectric substrate 112 enables hand-held device 102 to be compact and easily portable without sacrificing performance.

The metallization of antenna 106 is typically copper, chrome or gold, depending on substrate 112 used. In an embodiment where quartz or alumina is used as substrate 112, the typical thickness of the chrome and gold are 150 Angstroms and 2 microns, respectively. In an alternative embodiment, a hybrid integration of a pick-up coil antenna and tuning inductors, each on their own substrate and wire bonded, may be used. In another embodiment of the invention, a different antenna configuration, such as a square loop antenna or a hybrid integration of the hand-held powering and signal processing mechanism may be used. In yet another embodiment of the invention, a different antenna configuration, such as a hexagonal loop may be used.

In the embodiment illustrated in FIG. 1b, the strip conductor width 116 of antenna 106 is 0.508 mm, the gap 118 between the strips is 3.81 mm and the loop diameters 114a, 114b and 114c are 5.1, 4.3 and 3.6 cm, respectively. Antenna 106 is fabricated on 0.79 mm thick RT5580 Duroid® substrate 112 ($\epsilon_r$=2.22) with no ground plane. The dimension of antenna 106 is approximately 8.26×9.53 cm The inventive hand-held device exhibits an excellent safety factor because it relies on low RF power, for example 1 mW, and short interrogation times. This ensures minimum local heating of the body tissue surrounding biosensor 104 and ensures low absorption of radiation by sensitive body parts such as the eyes and brain.

FIG. 1c further illustrates hand-held device 102. According to FIG. 1c, device 102 includes a means for displaying information on a display screen 120 in hand-held device 102 and/or on a data storage and retrieval unit. The data storage and retrieval unit may include a separate computer, a portable device such as a Blue-Tooth enabled device complying with 802.11 standard or a wireless device. It should be apparent to those skilled in the art, that the data storage and retrieval unit may be used for displaying and/or processing data from hand-held device 102. Hand-held device 102 also includes slots 122, and 124 for devices, such as a memory stick or a Universal Serial Bus (USB) port, wireless card 128, key pads 130 and a battery compartment 126.

Figure 2A:
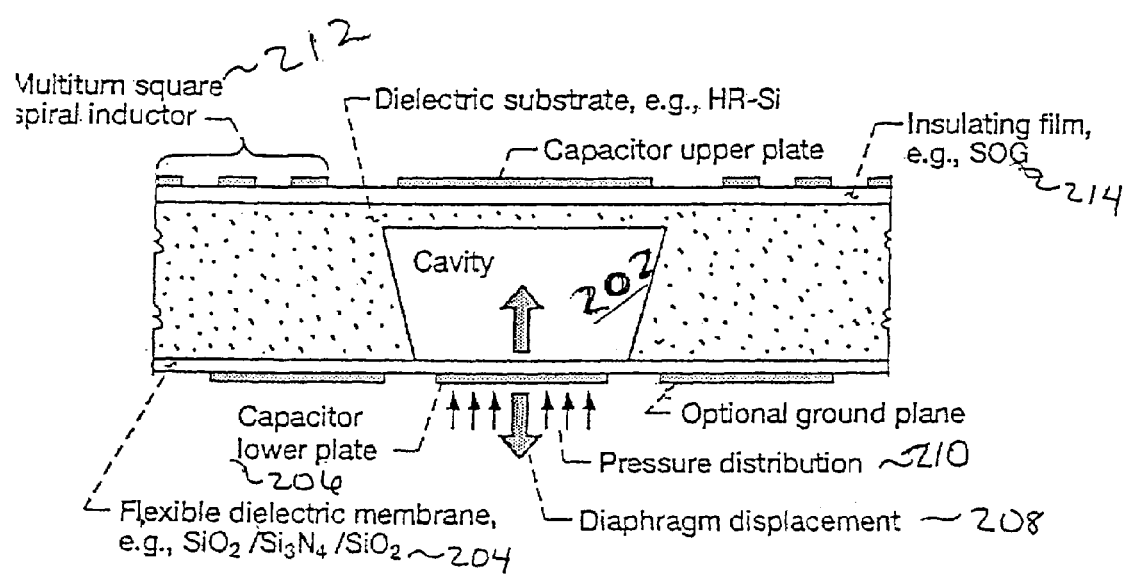
FIG. 2a illustrates the pressure sensor used in an embedded biosensor.

FIG. 2a illustrates pressure sensor 104 used in an in-vivo bio-sensor. Pressure sensor 104 includes a diaphragm suspended over a cavity 202 micromachined from a silicon wafer. In an embodiment, a tri-layer 204 of silicon dioxide and silicon nitride is used to realize the diaphragm. The diaphragm moves up and down 208 in response to mechanical pressure 210. Thin gold films on the diaphragm and on the lower surface of cavity 202 together form a parallel plate capacitor 206 whose capacitance changes with pressure. Pressure sensor 104 is of the capacitive type and is located in the annular region of an inductor 212. Inductor 212 acts as both an inductance and an antenna, thereby allowing sensor 104 to receive as well as radiate energy. In the receive mode, the inductance picks up energy and charges the microelectromechanical (MEMS) pressure sensor 104 diaphragm capacitance. In the transmit mode, the inductance and capacitance form a parallel resonant circuit and radiate energy through inductor 212 which acts as a planar spiral antenna. The performance of inductor 212 is improved by introducing an insulating layer 214, such as spin-on-glass.

Figure 2B:
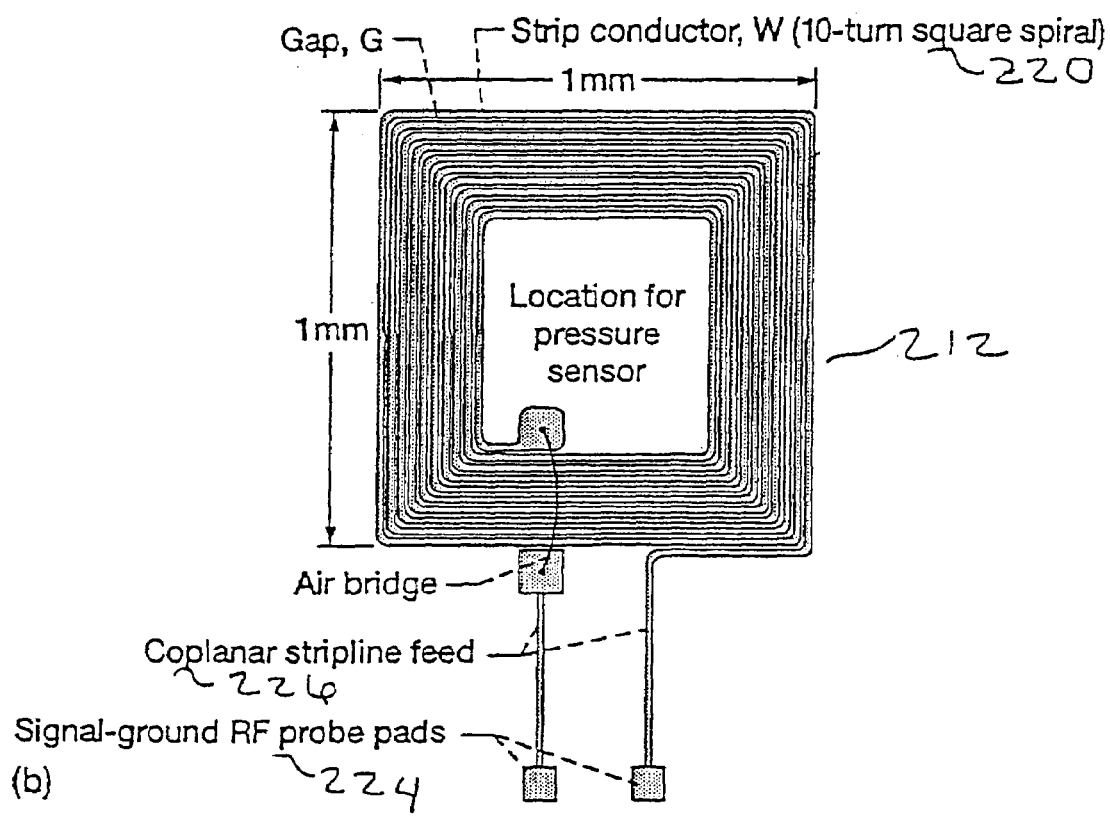
FIG. 2b illustrates the miniaturized spiral inductor/antenna circuit for powering and telemetry which is integrated with a bio-microelectromechanical (bio-MEMS) pressure sensor.

FIG. 2b illustrates the miniaturized spiral inductor/antenna circuit 212 for powering and telemetry which is integrated with a bio-microelectromechanical (bio-MEMS) pressure sensor 104. The outer dimensions of the inductor are approximately 1 by 1 mm and inductor 212 is fabricated using a high resistivity silicon wafer to reduce the attenuation of the signals. In an embodiment of pressure sensor 104, a miniaturized spiral inductor with inductance (L) of 150 nH and quality factor (Q) of about 10 is adequate for biomedical applications. It is well know to those skilled in the art that the inductance and quality factor are dependent on strip 220 and the separation or gap dimensions. Therefore, several inductors with strip and gaps dimensions in the range of 10 to 15 µm may be fabricated to optimize the circuit. According to an embodiment, chrome/gold metallization of 20 nm and 1.5 to 2.25 µm, respectively, may be used for circuits to minimize resistive losses. The frequency range over which the inductor/antenna 212 operates is between 200 to 700 MHz, consistent with the Federal Communications Commission (FCC) designated band. To facilitate characterization using signal-ground RF probe 224, the inductors are excited by a short length of coplanar stripline 226.

Figure 2C:
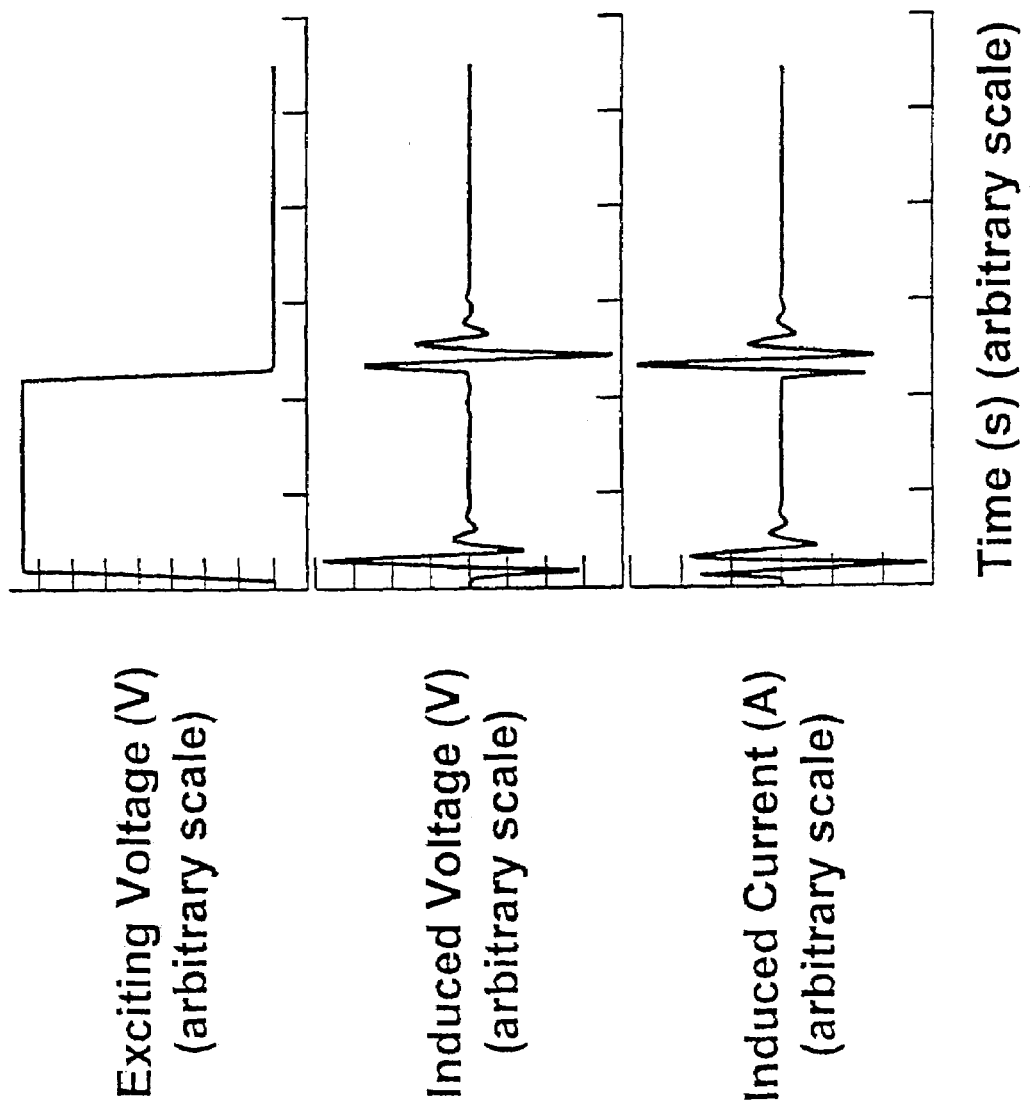
FIG. 2c illustrates a voltage and current waveform induced by the hand-held device during interrogation of the implanted sensor.

Returning to FIG. 1 which illustrates the overall implementation of the RF telemetry concept, to obtain a pressure reading, a pulse emitted by external hand-held device 102 initially interrogates implanted sensor 104. The pulse induces a voltage, at the rising and falling edges, in implanted sensor inductor 212, thus implementing contactless powering. The waveform of the induced voltage is a decaying sine wave. FIG. 2c illustrates a voltage and current waveform induced by the hand-held device during interrogation of the implanted sensor. The energy radiated by inductor 212 during these oscillations is picked up as a telemetry signal by receiving antenna 106 in hand-held device 102. Since the inductance is fixed, the frequency of the decaying sine wave is mainly determined by the capacitance of pressure sensor 104.

Figure 3A:
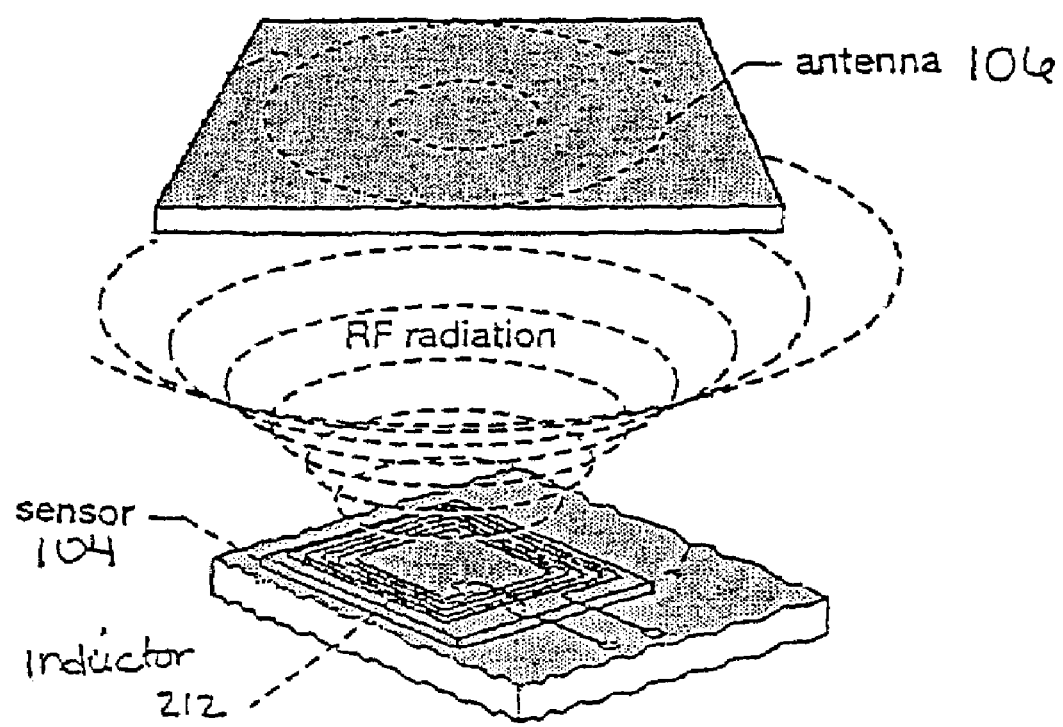
FIG. 3a illustrates the telemetry concept, wherein the pick-up antenna assembly is held at a fixed height and coaxial with the miniaturized transmitting inductor/antenna.
Figure 3B:
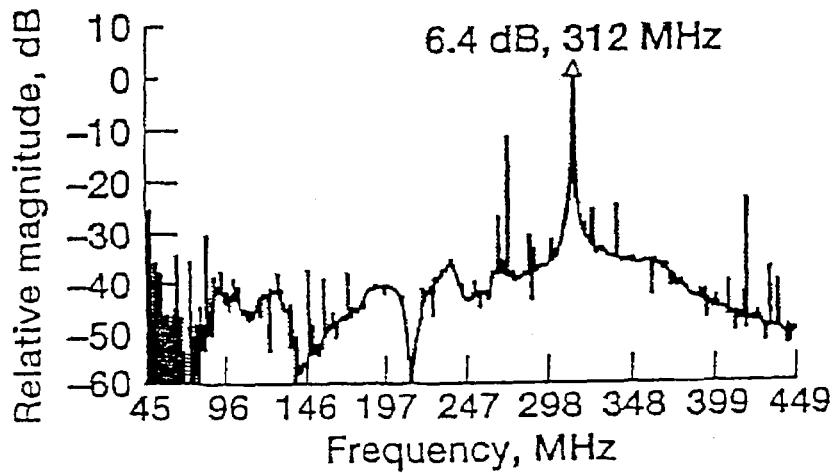
FIG. 3b illustrates measured received relative signal strength versus frequency for the pick-up antenna at the height of 5 cm.
Figure 3C:
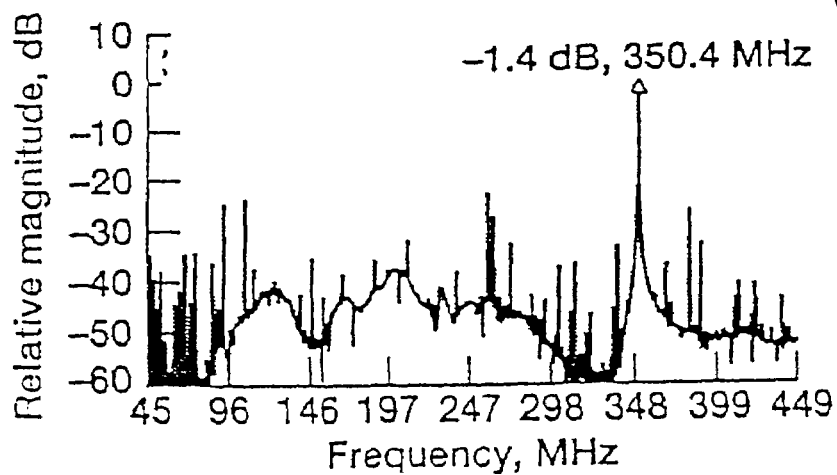
FIG. 3c illustrates measured received relative signal strength versus frequency for the pick-up antenna at the height of 10 cm.

FIGS. 3a, 3b and 3c further illustrate the telemetry concept. FIG. 3a illustrates the telemetry concept, wherein the pick-up antenna assembly is held at a fixed height and coaxial with the miniaturized transmitting inductor/antenna. The inductor/antenna is configured to resonate at about 330 MHz. When coupled to a signal source and the frequency is swept, inductor 212 radiates energy. The received power as measured at the coaxial connector port of receive antenna 106 for heights of 5 and 10 cm is shown in FIGS. 3b and 3c, respectively. Specifically, FIG. 3b illustrates measured received relative signal strength versus frequency for pick-up antenna 106 at the height of 5 cm and FIG. 3c illustrates measured received relative signal strength versus frequency for pick-up antenna 106 at the height of 10 cm. Note that the intensity of the maximum coupling drops as the separation increases, but even at 10 cm of separation, as illustrated in FIG. 3c, the signal strength of the received signal is still well defined.

Figure 4A:
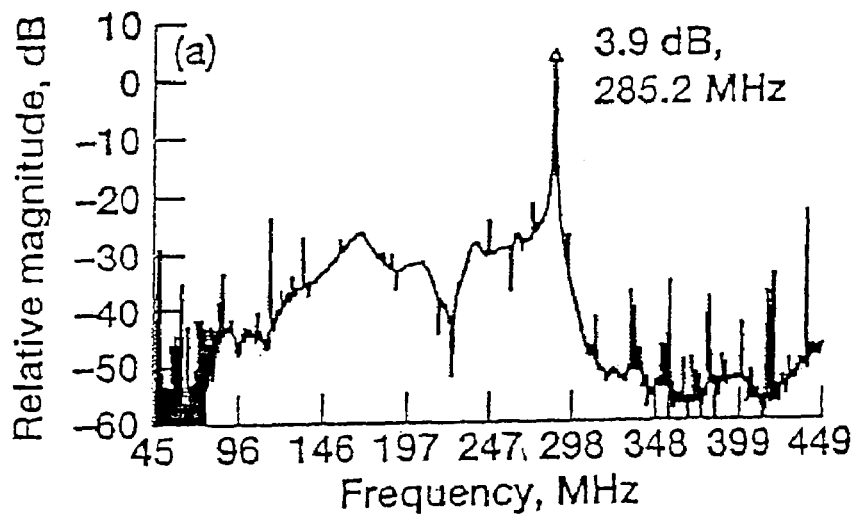
FIG. 4a illustrates the measured received relative signal strength versus frequency in the presence of a muscle tissue-like phantom with the pick-up antenna at the height of 5 cm.
Figure 4B:
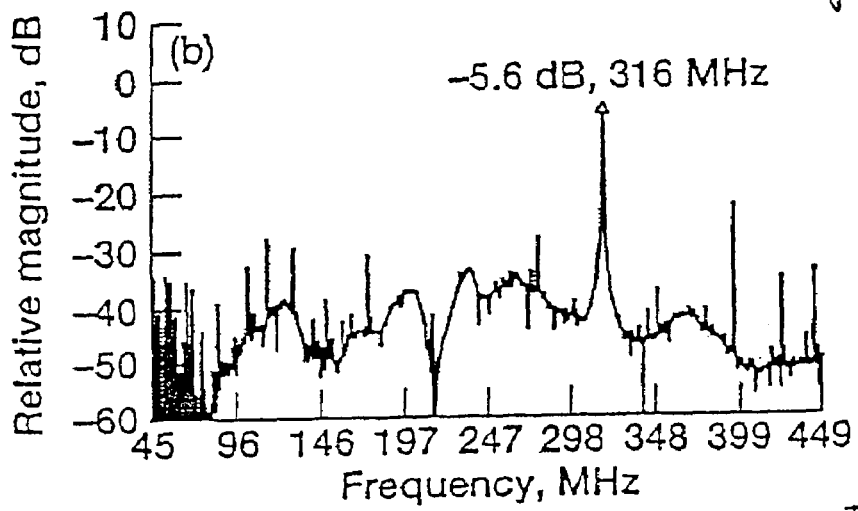
FIG. 4b illustrates the measured received relative signal strength versus frequency in the presence of a muscle tissue-like phantom with the pick-up antenna at the height of 10 cm.

FIG. 4a illustrates the measured received relative signal strength versus frequency in the presence of a muscle tissue-like phantom with the pick-up antenna at the height of 5 cm. FIG. 4b illustrates the measured received relative signal strength versus frequency in the presence of a muscle tissue-like phantom with the pick-up antenna at the height of 10 cm. Note that in FIG. 4a, at a separation distance of 5 cm, the magnitude of the relative signal strength only drops by 2.5 dB as compared to that in free space as illustrated by FIG. 3b. Likewise, the relative signal strength, illustrate in FIG. 4b, at 10 cm drops by only 4.2 dB as compared to that in free spaces as illustrated by FIG. 3c. As illustrated, FIGS. 4a and 4b simulate a typical operation condition for medical diagnostic applications where there are muscle tissues.

Figure 5A:
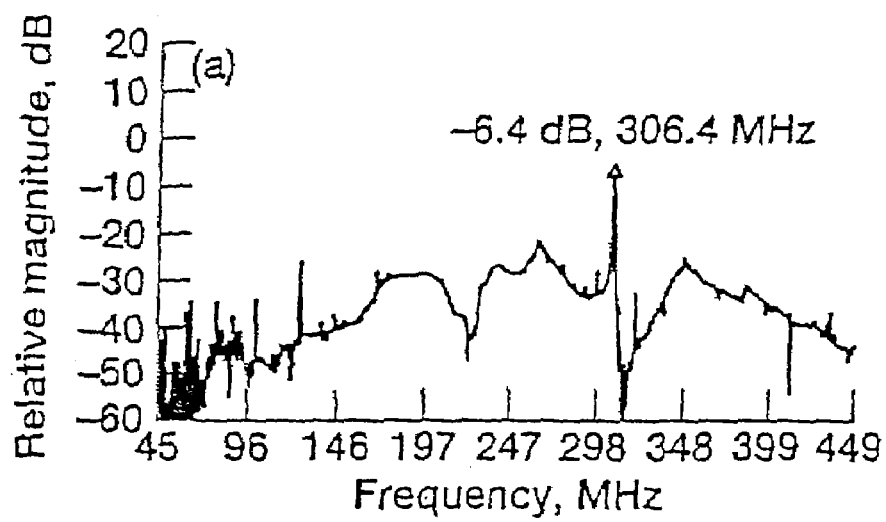
FIG. 5a illustrates the measured received relative signal strength versus frequency in the presence of a muscle tissue-like phantom with the packaged pick-up antenna at the height of 5 cm.
Figure 5B:
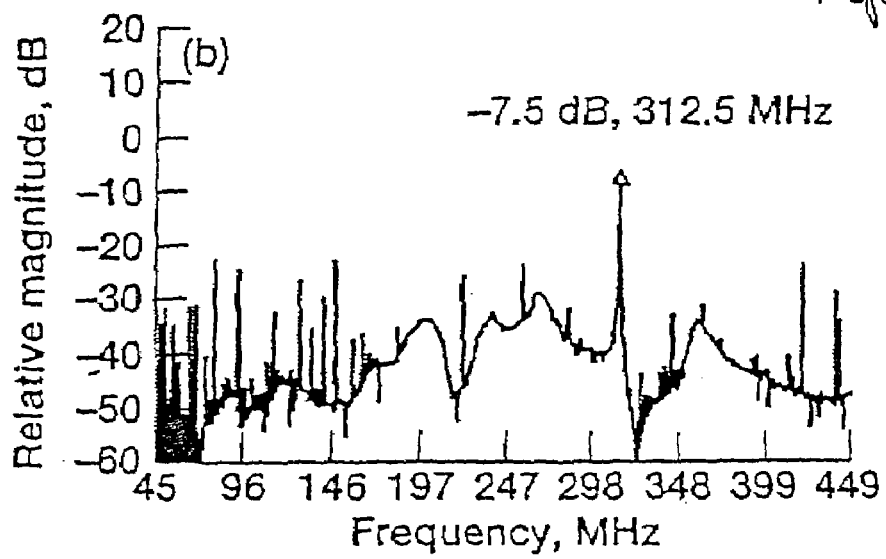
FIG. 5b illustrates the measured received relative signal strength versus frequency in the presence of a muscle tissue-like phantom with the packaged pick-up antenna at the height of 10 cm.

FIG. 5a illustrates the measured received relative signal strength versus frequency in the presence of a stratified dielectric media represented by muscle tissue-like phantom with the pick-up antenna packaged and at the height of 5 cm. FIG. 5b illustrates the measured received relative signal strength versus frequency in the presence of a stratified dielectric media represented by muscle tissue-like phantom with the pick-up antenna packaged and at the height of 10 cm. According to FIGS. 5a and 5b, the stratified dielectric media is used to simulate the hand-held device's ability to power and transmit data to and from in-vivo sensor 104. FIGS. 5a and 5b simulate the telemetry concept with a packaged receiving antenna typical of a hand-held device. The pick-up antenna is enclosed in a semi-rigid foam packaging material resembling that of the typical hand held device which is approximately 0.64 cm thick. As shown in FIGS. 5a and 5b, the relative signal strength is in the −6.4 to −7.5 dB range for the two separations.

The inventive system may therefore be used for monitoring medical conditions. The system may also be used for monitoring the health of astronauts inhabiting current and future space platforms, such as the Space Transportation System (the space shuttle), the International Space Station and other manned space platforms. The inventive fully integrated, compact hand-held device 102 for powering, interrogation and data retrieval from miniaturized biosensors 104 and actuators can establish significant electromagnetic coupling with a low radiating RF power inductor/antenna concept even at separations of up to ten centimeters. The invention thus allows for activation of biosensor 104 only when sensor interrogation and data retrieval are required. This allows sensor 104 to be in the off-state most of the time, thereby extending its useable life as compared to a battery-based sensor. Additionally, the compact size of hand-held device 102 allows for easy storage and portability. Thus allowing a patient using hand-held device 102 to self-diagnose anywhere. Moreover, since there are no feed-through leads required for powering and RF telemetry of sensor 104, the invention allows for enhanced mobility and eliminates the need for external implantable devices.

The foregoing description has been directed to specific embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A compact, hand-held device for wireless powering, interrogation and data retrieval from an implanted sensor, the hand-held device comprising:
   an antenna for powering the implanted sensor and for receiving data from the implanted sensor to the hand-held device for at least one of storage, display and analysis,
   wherein the hand-held device establishes electromagnetic coupling at radio frequency with an inductor in the implanted sensor at a predefined separation and the hand-held device allows for the antenna to power, interrogate and retrieve data from the implanted sensor, the hand-held device being at a predefined distance from a human body housing the implanted sensor,
   wherein the antenna is a multi-turn circular loop antenna whose impedance at approximately 330 MHz is matched to an input impedance from an amplifier in a receiver to increase sensitivity.

2. The hand-held device according to claim 1, wherein the hand-held device allows for activation of the implanted sensor only during interrogation and data retrieval.

3. The hand-held device of claim 1, wherein the antenna powers, interrogates and retrieves the data from the implanted sensor through body fluid and tissue.

4. The hand-held device of claim 1, wherein the antenna is configured to pick up signals that are vertically, horizontally or slant polarized.

5. The hand-held device of claim 1, further comprising electronic circuitry for at least one of logging, displaying and downloading the data.

6. The hand-held device of claim 1, wherein the antenna acts as a receive antenna during an interrogation mode and picks up radio frequency radiation as a telemetry signal from the implanted sensor when the antenna is placed outside the human body housing the implanted sensor and in a predefined proximity to an emitter in the implanted sensor.

7. The hand-held device of claim 1, wherein an antenna assembly comprises:
   an integrated amplifier to enable communications across predefined implant depths;
   integrated surface mount inductors for impedance tuning of the antenna; and
   at least one signal processing mechanism.

8. The hand-held device of claim 1, wherein the antenna is printed on a substrate with a central annular region, thereby facilitating housing of signal processing circuits and enabling a predefined height and profile of the hand-held device.

9. The hand-held device of claim 8, wherein the substrate is made of a low loss radio frequency dielectric material.

10. The hand-held device of claim 8, wherein design of the antenna depends on dielectric properties of the substrate.

11. The hand-held device of claim 1, wherein the antenna is a pick-up coil antenna that is integrated with tuning inductors, whereby the antenna is on a same substrate as the tuning inductors and the antenna is wire-bonded with the tuning inductors.

12. The hand-held device according to claim 1, wherein the antenna is a multi-turn square loop antenna.

13. The hand-held device according to claim 1, wherein the antenna is a multi-turn hexagonal loop antenna.

14. A method for obtaining at least one reading in a hand-held device from an implanted sensor, the method comprising the steps of:
   emitting a pulse from an external hand-held device within a predefined proximity to a receptor in an implanted sensor, wherein the pulse is used for at least interrogating the implanted sensor;
   powering the implanted sensor by inducing a voltage, via the pulse, in an inductor embedded in the implanted sensor;
   retrieving energy as a telemetry signal radiated by the inductor by an antenna in the hand-held device; and
   receiving data, by the antenna, from the implanted sensor for at least one of storage, display or analysis, wherein
   wherein the antenna is a multi-turn circular loop antenna whose impedance at approximately 330 MHz is matched to an input impedance from an amplifier in a receiver to increase sensitivity.

15. The method of claim 14, wherein the step of emitting is performed only during interrogation and data retrieval.

16. The method of claim 14, wherein the step of retrieving comprises retrieving signals that are vertically, horizontally or slant polarized.

17. The method of claim 14, further comprising the step of performing at least one of logging, displaying and downloading data from the hand-held device.

18. A hand-held device for wireless powering, interrogation and data retrieval from an implanted sensor, the hand-held device comprising:
   an antenna for powering an implanted sensor and for retrieving data from the implanted sensor to the hand-held device for at least one of storage, display or analysis, wherein an antenna assembly comprises an integrated amplifier to enable communications across predefined implant depths, integrated surface mount inductors for impedance tuning of the antenna and at least one signal processing mechanism,
   wherein the hand-held device establishes electromagnetic coupling at radio frequency with an inductor in the implanted sensor at a predefined separation and an antenna geometry allows for the antenna to power, interrogate and retrieve data from the implanted sensor, the hand-held device being at a predefined distance from a human body housing the implanted sensor, and wherein the hand-held device allows for activation of the implanted sensor only during interrogation and data retrieval, wherein wherein the antenna is a multi-turn circular loop antenna whose impedance at approximately 330 MHz is matched to an input impedance from an amplifier in a receiver to increase sensitivity.

19. A hand-held device for wireless powering, interrogation and data retrieval from an implanted sensor, the hand-held device comprising:

a multi-turn loop antenna printed on a dielectric substrate for powering an implanted sensor, the antenna being used for retrieving data from the implanted sensor to the hand-held device for at least one of storage, display or analysis, wherein an antenna assembly comprises an integrated amplifier to enable communications across larger implant depths, integrated surface mount inductors for impedance tuning of the antenna and at least one signal processing mechanism, wherein the hand-held device establishes electromagnetic coupling at radio frequency with an inductor in the implanted sensor at a predefined separation and an antenna geometry allows for the antenna to power, interrogate and retrieve data from the implanted sensor, the hand-held device being at a predefined distance from a human body housing the implanted sensor, and wherein the hand-held device allows for activation of the implanted sensor only during interrogation and data retrieval, wherein wherein the antenna is a multi-turn circular loop antenna whose impedance at approximately 330 MHz is matched to an input impedance from an amplifier in a receiver to increase sensitivity.

20. An apparatus for obtaining at least one reading in a hand-held device from an implanted sensor, the apparatus comprising:

emitting means for emitting a pulse from an external hand-held device within a predefined proximity to a receptor in an implanted sensor, wherein the pulse is used for at least interrogating the implanted sensor;

powering means for powering the implanted sensor by inducing a voltage, via the pulse, in an inductor embedded in the implanted sensor;

receiving means for receiving energy as a telemetry signal radiated by the inductor by an antenna in the hand-held device; and retrieving means for retrieving data, by the antenna, from the implanted sensor to the hand-held device for at least one of storage, display or analysis, wherein wherein the antenna is a multi-turn circular loop antenna whose impedance at approximately 330 MHz is matched to an input impedance from an amplifier in a receiver to increase sensitivity.

* * * * *